United States Patent
Kim et al.

(10) Patent No.: US 10,301,332 B2
(45) Date of Patent: May 28, 2019

(54) METHOD OF SELECTIVELY RELEASING NITRIC OXIDE DEPENDING ON CHANGE IN PH USING CALCIUM PHOSPHATE

(71) Applicants: INSTITUTE FOR BASIC SCIENCE, Daejeon (KR); POSTECH ACADEMY-INDUSTRY FOUNDATION, Gyeongsangbuk-do (KR)

(72) Inventors: Won Jong Kim, Gyeongsangbuk-do (KR); Jihoon Kim, Gyeongsangbuk-do (KR); Hyung Woo Choi, Gyeongsangbuk-do (KR)

(73) Assignees: Institute for Basic Science, Daejeon (KR); Postech Academy-Industry Foundation, Gyeongsangbuk-do (KR)

( * ) Notice: Subject to any disclaimer, the term of this patent is extended or adjusted under 35 U.S.C. 154(b) by 0 days.

(21) Appl. No.: 15/359,474

(22) Filed: Nov. 22, 2016

(65) Prior Publication Data

US 2017/0145040 A1 May 25, 2017

(30) Foreign Application Priority Data

Nov. 23, 2015 (KR) .................. 10-2015-0163839

(51) Int. Cl.
| | |
|---|---|
| *C07F 7/18* | (2006.01) |
| *B01J 20/04* | (2006.01) |
| *B01J 20/22* | (2006.01) |
| *A61K 33/00* | (2006.01) |
| *C01B 21/24* | (2006.01) |
| *A61K 31/655* | (2006.01) |
| *A61K 31/695* | (2006.01) |
| *A61K 47/54* | (2017.01) |
| *A61K 47/69* | (2017.01) |
| *B82Y 5/00* | (2011.01) |

(52) U.S. Cl.
CPC .......... *C07F 7/1804* (2013.01); *A61K 31/655* (2013.01); *A61K 31/695* (2013.01); *A61K 33/00* (2013.01); *A61K 47/54* (2017.08); *A61K 47/6923* (2017.08); *A61K 47/6929* (2017.08); *B01J 20/048* (2013.01); *B01J 20/22* (2013.01); *C01B 21/24* (2013.01); *B82Y 5/00* (2013.01)

(58) Field of Classification Search
CPC .... C01B 21/24; A61K 33/00; A61K 47/6923; A61K 47/6929; A61K 31/655; A61K 31/695; A61K 47/54; B01J 20/048; B01J 20/22; B82Y 5/00
See application file for complete search history.

(56) References Cited

U.S. PATENT DOCUMENTS 8,389,017 B1 * 3/2013 Starling ................ A61K 9/501
424/489

FOREIGN PATENT DOCUMENTS

| JP | 2008073098 A | 4/2008 |
| KR | 101351130 B1 | 1/2014 |

OTHER PUBLICATIONS

Koh et al. Appl. Mater. Interfaces, 2013, 5, 7956-7964.*
Storm et al. Appl. Mater. INterfaces, 2013, 5, 4904-4912.*
Rim, H. et al., "pH-Tunable Calcium Phosphate Covered Mesoporous Silica Nanocontainers for Intracellular Controlled Release of Guest Drugs," Angewandte Chemie International Edition, vol. 50, No. 38, Sep. 12, 2011, Published Online Aug. 8, 2011, 5 pages.
Kim, J. et al., "A platform for nitric oxide delivery," Journal of Materials Chemistry B, vol. 2, No. 4, Jan. 28, 2014, Published Online Oct. 29, 2013, 16 pages.
Michaylova, V. et al., "Photometric determination of micro amounts of calcium with arsenazo III," Analytica Chimica Acta, vol. 53, No. 1, Jan. 1971, 5 pages.

* cited by examiner

*Primary Examiner* — Johann R Richter
*Assistant Examiner* — Genevieve S Alley
(74) *Attorney, Agent, or Firm* — McCoy Russell LLP

(57) ABSTRACT

Provided is a method of controlling release of nitric oxide, and more particularly, to a method of selectively releasing nitric oxide depending on a change in pH using calcium phosphate.
The method of selectively releasing nitric oxide according to the present invention may stably deliver nitric oxide to a desired site, and induce release of nitric oxide by a change in pH, thereby making it possible to improve a therapeutic effect while preventing a loss of nitric oxide.

7 Claims, 10 Drawing Sheets

(pH 7.4)

(pH 5.0)

1) Pure CaP, 2) CaP_AEATS, 3) CaP-NO (XRD)

1) AEATS, 2) Pure CaP, 3) CaP_AEATS, 4) CaP-NO

1) Pure CaP, 2) CaP_AEATS, 3) CaP-NO pH 7.4 AEATS

METHOD OF SELECTIVELY RELEASING NITRIC OXIDE DEPENDING ON CHANGE IN PH USING CALCIUM PHOSPHATE

CROSS-REFERENCE TO RELATED APPLICATIONS

This application claims priority under 35 U.S.C. § 119 to Korean Patent Application No. 10-2015-0163839, filed on Nov. 23, 2015, in the Korean Intellectual Property Office. The disclosure of which is incorporated herein by reference in its entirety for all purposes.

TECHNICAL FIELD

The following disclosure relates to a method of controlling release of nitric oxide, and more particularly, to a method of selectively releasing nitric oxide depending on a change in pH using calcium phosphate.

BACKGROUND

Nitric oxide, which is a radical molecule having high reactivity, is a gas synthesized by nitric oxide synthase in cells and has an important function as a bioactive compound in the body. Particularly, nitric oxide has been known to be associated with various physiological phenomena such as a neurotransmission system, a cardiovascular system, an immune system, and the like, and diseases.

For example, nitric oxide has contrary therapeutic effects in accordance with a concentration and a release time thereof. It has been known that when high-concentration nitric oxide is released for a short time, an anti-cancer effect and anti-bacterial effect are exhibited, and when a small amount of nitric oxide is released for a long period of time, nitric oxide is associated with wound treatment, cell growth, angiogenesis, and the like. However, since nitric oxide exists in a gas form, there is a large limitation in effectively delivering nitric oxide.

Diazeniumdiolate, which is a representative functional group releasing nitric oxide, is also referred to as NONOate, and may be represented by General Formula, RR'N—N(O)=NOR". Diazeniumdiolate may be stably stored in a solid form, has high solubility in water, and is decomposed under the body temperature and pH conditions, and a release form thereof is variously changed depending on pH. Diazeniumdiolate may easily produce nitric oxide and release a relatively large amount of nitric oxide, but there is a problem in that diazeniumdiolate releases nitric oxide while simultaneously contacting water.

In order to overcome this problem, a technology of releasing nitric oxide by external stimuli has been developed, but a case in which both the external stimuli and biocompatible product are applied is significantly rare. The present applicant tried to introduce a novel system of inducing release of nitric oxide by a change in pH while blocking a contact with the outside by introducing calcium phosphate, which is a biocompatible material. Further, the present applicant tried to develop a system of more stably delivering nitric oxide while minimizing a loss of nitric oxide generated in a delivery process.

RELATED ART DOCUMENT

Patent Document (Patent Document 1) Korean Patent Publication No. 10-1351130

SUMMARY

An embodiment of the present invention is directed to providing nitric oxide releasing particles capable of stably delivering an excessive amount of nitric oxide to a desired site.

Another embodiment of the present invention is directed to providing a method of selectively releasing nitric oxide capable of improving a therapeutic effect by inducing release of nitric oxide from nitric oxide releasing particles only under a restrictive pH condition in order to solve a problem of a diazeniumdiolate functional group which releases nitric oxide while simultaneously contacting water.

In one general aspect, nitric oxide releasing particles includes a silane coupling agent containing a secondary amine group, and calcium phosphate.

In another general aspect, a method of preparing nitric oxide releasing particles includes: a) forming calcium phosphate in a solution in which a silane coupling agent containing a secondary amine group is contained; and b) adding nitric oxide gas thereto to form a diazeniumdiolate functional group.

In another general aspect, there is provided a method of selectively releasing nitric oxide, wherein nitric oxide is released by adjusting a pH of the prepared nitric oxide releasing particles to 5.0 to 7.4.

DETAILED DESCRIPTION OF EMBODIMENTS

Figure 1:
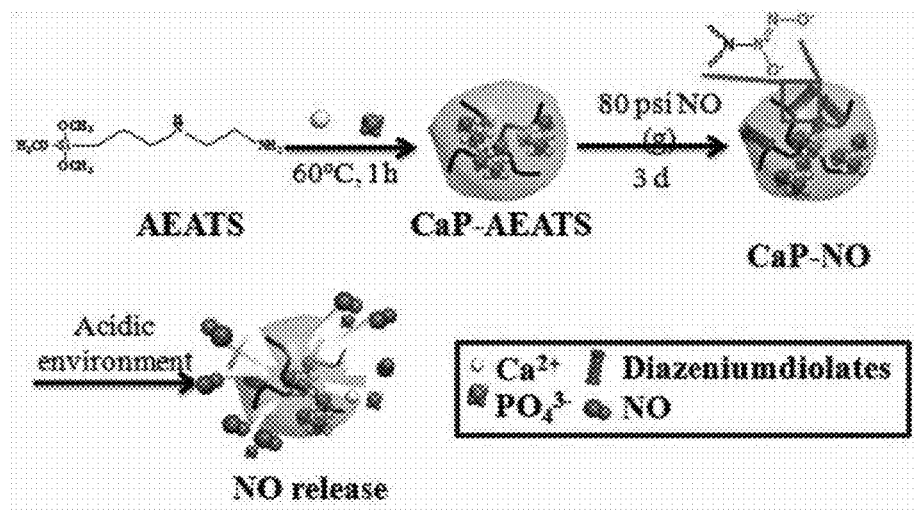
FIG. 1 illustrates a process of preparing nitric oxide releasing particles according to an exemplary embodiment of the present invention.

Hereinafter, the present invention will be described in detail with reference to the accompanying drawings. Here, technical terms and scientific terms used in the present specification have the general meaning understood by those skilled in the art to which the present invention pertains unless otherwise defined, and a description for the known function and configuration obscuring the present invention will be omitted in the following description.

The present invention relates to nitric oxide releasing particles containing a silane coupling agent containing a secondary amine group and calcium phosphate, and a method of selectively releasing nitric oxide using the same.

In the present invention, the term "selective release" means that nitric oxide may be released under a specific condition in the body, that is, releasing particles inserted by an artificial implantable material or medical device, or the like, release nitric oxide under the specific condition. This means that these nitric oxide releasing particles do not unpredictably and intermittently release nitric oxide, nor explosively release nitric oxide.

Hereinafter, the nitric oxide releasing particles according to the present invention will be described in detail.

In the present invention, the nitric oxide releasing particles may contain a functional group capable of releasing nitric oxide, wherein the functional group may be "diazeniumdiolate".

The diazeniumdiolate functional group may be obtained by reacting nitric oxide with a secondary amine as illustrated in the following Reaction Formula 1. Further, the diazeniumdiolate functional group may be represented by General Formula, RR'N—N(O)=NOR".

[Reaction Formula 1]

$$\begin{array}{c} R^1 \\ \diagdown \\ N-H \\ \diagup \\ R^2 \end{array} + 2NO \xrightleftharpoons[H^+]{} \begin{array}{c} R^1 \\ \diagdown \\ N-N \\ \diagup \\ R^2 \end{array} \begin{array}{c} O^- \\ \oplus \\ N-N \\ \diagdown \\ N-O^- \end{array} + H^+$$

Since each of the diazeniumdiolate functional groups releases two nitric oxide molecules, when the diazeniumdiolate functional group is contained in the releasing particles, the nitric oxide releasing particles may generate relatively high-concentration nitric oxide. However, since the diazeniumdiolate functional group releases nitric oxide while simultaneously contacting with water, a gate keeper system of controlling release of nitric oxide through external stimulus is required for efficient nitric oxide delivery. Therefore, according to the present invention, only when the nitric oxide releasing particles are exposed to the specific condition in the body, a reaction of the diazeniumdiolate functional group may occur to release nitric oxide.

In the diazeniumdiolate in Reaction Formula 1, nitric oxide release characteristics may be adjusted by adjusting functional groups corresponding to $R^1$ and $R^2$. Further, since diazeniumdiolate has an oxygen atom on which an electron density is concentrated, the diazeniumdiolate may further contain another active material in addition to the nitric oxide in a form of a conjugate in which another pharmacological active material is linked to the oxygen atom of diazeniumdiolate.

In the exemplary embodiment of the present invention, the silane coupling agent containing the secondary amine group may be used. In the silane coupling agent as describe above, the secondary amine group may react with nitric oxide to form the diazeniumdiolate functional group.

The silane coupling agent according to the present invention has a structure having at least two kinds of functional groups having different reactivities, and when the alkoxysilyl (Si—OR) functional group in the structure is hydrolyzed, the alkoxysilyl functional group may be converted to a silanol group to bind to an inorganic material, and may serve to connect an organic material and the inorganic material to each other.

The silane coupling agent may be represented by the following Chemical Formula 1.

[Chemical Formula 1]

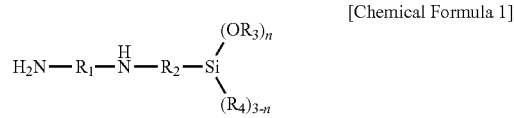

(In Chemical Formula 1, $R_1$ and $R_2$ are each independently a (C1-C12)alkylene group, $R_3$ and $R_4$ are each independently a (C1-C4)alkyl group, and n is 1 to 3).

More preferably, in the present invention, the desired effect of the present invention may be obtained using N-(2-aminoethyl)-3-aminopropyl trimethoxysilane (AEATS), but the present invention is not limited thereto.

According to the exemplary embodiment of the present invention, an amount of diazeniumdiolate functional group introduced into the nitric oxide releasing particles is not particularly limited, but a conversion rate of the secondary amine functional group to diazeniumdiolate is about 50% or more, but is not limited thereto. Generally, it is preferable that the conversion rate to diazeniumdiolate is increased as high as possible, but ultimately, a content of the diazeniumdiolate functional group may be adjusted by suitably adjusting a reaction condition depending on final nitric oxide release characteristics to be desired by an average person skilled in the art.

In the present invention, release of nitric oxide depending on a change in pH may be controlled using calcium phosphate as the gate keeper system controlling release of nitric oxide. In the case of calcium phosphate used in the present invention, since calcium phosphate is decomposed when a pH is decreased, nitric oxide may be selectively released.

Calcium phosphate used in the present invention indicates a phosphate salt of calcium, and preferably, hydroxyapatite may be used.

Since hydroxyapatite ($Ca_{10}(PO_4)_6(OH)_2$), which is a bio-inorganic compound, has a structure most similar to that of the bond in a human body and binds to a polymer to have excellent bone regeneration capacity, bioactivity, biocompatibility, and biodegradability as a substitute for bone tissue, hydroxyapatite may be mainly utilized in tissue engineering. In the present invention, since calcium phosphate has characteristics that it is decomposed when the pH is decreased, calcium phosphate may be used as the gate keeper system effectively controlling release of hydroxyapatite.

The present invention may provide a method of preparing nitric oxide releasing particles including:
a) forming calcium phosphate in a solution in which a silane coupling agent containing a secondary amine group is contained; and
b) injecting nitric oxide gas thereinto to form a diazeniumdiolate functional group.

As the silane coupling agent, a silane coupling agent represented by the following Chemical Formula 1 may be used.

[Chemical Formula 1]

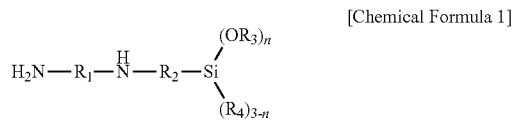

(In Chemical Formula 1, $R_1$ and $R_2$ are each independently a (C1-C12)alkylene group, $R_3$ and $R_4$ are each independently a (C1-C4)alkyl group, and n is 1 to 3).

In step a), calcium phosphate may be formed by a wetting method of preparing a water-soluble phosphate salt and a calcium salt using a liquid medium.

The phosphate salt used in the present invention is not particularly limited, but phosphoric acid ($H_3PO_4$), sodium dihydrogen phosphate ($NaH_2PO_4$), sodium hydrogen phosphate ($Na_2HPO_4$), potassium dihydrogen phosphate ($KH_2PO_4$), potassium hydrogen phosphate ($K_2HPO_4$), ammonium dihydrogen phosphate ($NH_4H_2PO_4$), ammonium hydrogen phosphate (($NH_4)_2HPO_4$), or the like, may be used. Further, as the calcium salt, calcium nitrate ($Ca(NO_3)_2$), calcium carbonate ($CaCO_3$), calcium chloride ($CaCl_2$), calcium hydroxide ($Ca(OH)_2$), calcium acetate ($Ca(CH_3COO)_2$), or the like, may be used.

Further, according to the exemplary embodiment of the present invention, it is preferable that the solution in step a) further contains a liquid medium. As the liquid medium, water, alcohol, or a mixture thereof may be used. Here, it is preferable that water is purified water or distilled water. It is preferable that a monohydric alcohol such as methanol, ethanol, propanol, or the like is used as the alcohol.

A sequence of addition in step a) is not limited, but in order to prevent formation of by-products, it is preferable that after the silane coupling agent is dissolved in the phosphate solution, a nitrate solution is added thereto, and mixed.

The calcium phosphate formed in the present invention may be preferably hydroxyapatite ($Ca_{10}(PO_4)_6(OH)_2$).

Hydroxyapatite according to the present invention is sensitive to a pH, such that a precipitate may be formed at about pH 12, but as a reaction proceeds, the pH is decreased, and thus, at an end stage of the reaction, the precipitate may be formed at about pH 7 to 11. A hydroxyapatite precipitate does not secure sufficient calcium in a crystalline structure thereof in a region in which the pH is 7 or less, calcium deficient hydroxyapatite, that is, hydroxyapatite of which a structure is destructed may be formed.

According to the present invention, in step a), the pH may be adjusted to 7 to 11.

A reaction of the mixed solution may be carried out at about 50 to 90° C. Since a reaction time is associated with the kind of calcium phosphate compound to be formed, the reaction time needs to be suitably selected in consideration of the kind of calcium phosphate compound. Since the reaction time significantly affects a size of particles, it is preferable that the reaction time is 30 to 90 minutes. When the reaction is terminated, powder may be prepared by filtering the solution, separating the precipitate, washing the separated precipitate, and drying the washed precipitate.

The injecting of the nitric oxide gas to the powder prepared in step a) to form the diazeniumdiolate functional group is as follows.

The diazeniumdiolate functional group may be obtained by reacting nitric oxide gas with a secondary amine as illustrated in the following Reaction Formula 1.

[Reaction Formula 1]

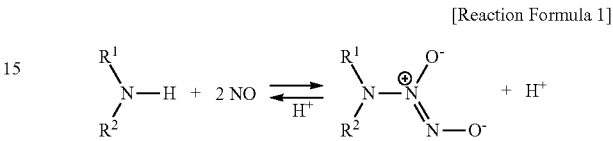

In the present invention, before the nitric oxide gas is injected, a purging step using argon gas may be performed at a pressure of 10 psi to 30 psi 1 to 3 times.

Next, the nitric oxide gas may be injected to a reactor subjected to the purging step at a pressure of 40 psi to 200 psi, preferably, 80 psi to 150 psi. The nitric oxide releasing particles containing the diazeniumdiolate functional group may be prepared by performing the reaction for 1 to 5 days after the nitric oxide gas is injected.

The present invention may provide a method of selectively releasing nitric oxide wherein nitric oxide is released by adjusting a pH of the prepared nitric oxide releasing particles to 5.0 to 7.4.

Further, the nitric oxide releasing particles according to the present invention may additionally contain a pharmacologically effective material therein or on surfaces thereof. Therefore, the nitric oxide releasing particles may be used for additional pharmacological effects in addition to a nitric oxide effect.

The pharmacologically effective material may be fixed in a form of a conjugate in which the pharmacologically effective material is chemically linked to the nitric oxide releasing particles by chemical bonds to thereby be contained in the nitric oxide releasing particles, or may be contained in the nitric oxide releasing particles in a state in which the pharmacologically effective material is simply dispersed without a chemical bond. For example, the pharmacologically effective material may be covalently bonded to an oxygen atom of the diazeniumdiolate functional group to thereby be fixed thereto. As another example, the pharmacologically effective material or a derivative thereof that is positively charged may be electrically bonded to the diazeniumdiolate functional group that is negatively charged.

The pharmacologically effective material is not limited, but may include, preferably, a material for preventing thrombosis or blood coagulation, an antioxidant, an anti-inflammatory drug, a material for promoting wound healing, an anti-cancer drug, an antibacterial agent, or the like, such that the therapeutic effect of nitric oxide in addition to the therapeutic effect of the drug may be simultaneously exhibited.

Hereinafter, the present invention will be described in detail through Examples. However, the following Examples are only to specifically explain the present invention. Therefore, the present invention is not limited thereto.

Example 1

Preparation of Nitric Oxide Releasing Particles

1. Reaction of Calcium Phosphate and Silane Coupling Agent (CaP-AEATS)

After 22 μg of N-(N-(2-aminoethyl)-3-aminopropyl trimethoxysilane (AEATS) was dissolved in 10 ml of 0.1M $(NH_4)_2HPO_4$, 20 ml of 0.1M $Ca(NO_3)_2 \cdot 4H_2O$ was added dropwise thereto (Ca:AEATS=10:1). A pH was adjusted to 9 by adding ammonia water thereto, and a reaction was carried out at 60° C. for 1 hour.

A precipitate was separated by centrifugation at 3000 rpm for 15 minutes, and the separated precipitate was washed with deionized water three times. The resultant was freeze-dried for 48 hours, thereby obtaining CaP-AEATS.

2. Substitution of Diazeniumdiolate Functional Group (CaP—NO)

After 10 mg of the obtained CaP-AEATS was dissolved in 3 ml of 0.5M NaOMe/MeOH, the solution was put into a high-pressure reactor. After the reactor was purged with Ar gas (20 psi) two times, the solution was reacted with NO gas (80 psi) for 3 days. The CaP—NO having a diazeniumdiolate functional group capable of releasing nitric oxide was separated by centrifugation at 4000 rpm for 10 minutes, and then, the remaining solvent was removed by vacuum-drying.

Comparative Example 1

Preparation of Pure CaP

After 10 ml of 0.1M $(NH_4)_2HPO_4$ was prepared, 20 ml of 0.1M $Ca(NO_3)_2 \cdot 4H_2O$ was added dropwise thereto. A pH was adjusted to 9 by adding ammonia water thereto, and a reaction was carried out at 60° C. for 1 hour.

A precipitate was separated by centrifugation at 3000 rpm for 15 minutes, and the separated precipitate was washed with deionized water three times. The resultant was freeze-dried for 48 hours, thereby obtaining CaP-AEATS.

[Evaluation of Characteristics]

A nitric oxide release behavior depending on the change in pH was confirmed through a nitric oxide detection device. Existence of nitric oxide, biodegradation characteristics of calcium phosphate were confirmed through transmission electron microscopy, X-ray diffraction analysis, ultraviolet-visible (UV-Vis) spectroscopy, Fourier transform infrared spectroscopy, detection of calcium ions, and the like.

Further, in order to confirm biocompatibility, whether or not the material has toxicity was confirmed using Hela cells obtained in uterine cervical cancer tissue and fibroblast cells (NIH-3T3).

1. Transmission Electron Microscopy

Figure 2:
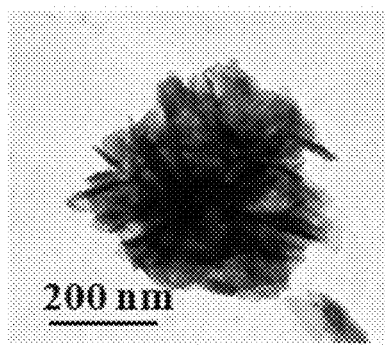
FIG. 2 illustrates a result obtained by measuring the nitric oxide releasing particles according to the exemplary embodiment of the present invention using transmission electron microscopy.
Figure 2:
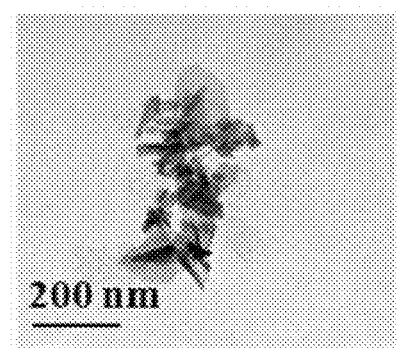

FIG. 2 illustrates a result obtained by confirming biodegradability of CaP—NO particles using a transmission electron microscope (TEM, JEOL JEM-1011 Japan).

As a result of observing a change in particle size of the CaP—NO particles at pH 7.4 and pH 5, it was observed that the particle size (about 200 nm) of the CaP—NO particles was maintained at pH 7.4, but it was confirmed that the particle size was significantly decreased at pH 5 due to biodegradability of hydroxyapatite.

2. Powder X-Ray Diffraction (XRD) Analysis

Figure 3:
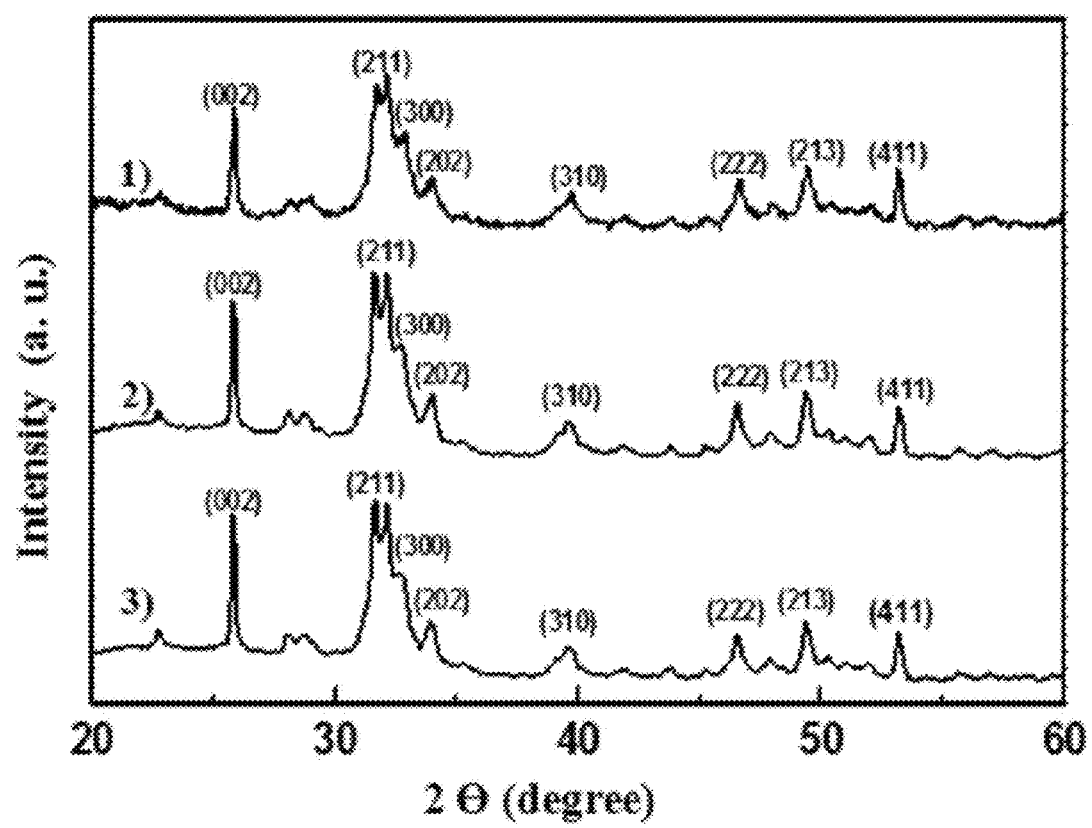
FIG. 3 is a graph illustrating a result obtained by analyzing crystalline structures of the nitric oxide releasing particles according to the exemplary embodiment of the present invention using powder X-ray diffraction (XRD) analysis.

FIG. 3 illustrates a result obtained by observing crystalline structures of pure CaP, CaP-AEATS, and CaP—NO through Powder XRD (using Cu Kα1 radiation (λ=1.54 A) from Rigaku SmartLab at 40 kV and 30 mA) analysis.

As a result of observing changes in crystalline structures of CaP-AEATS and CaP—NO in comparison with pure CaP, it was confirmed that even though AEATS and NO were added thereto, a crystalline structure of hydroxyapatite was not changed.

Figure 4:
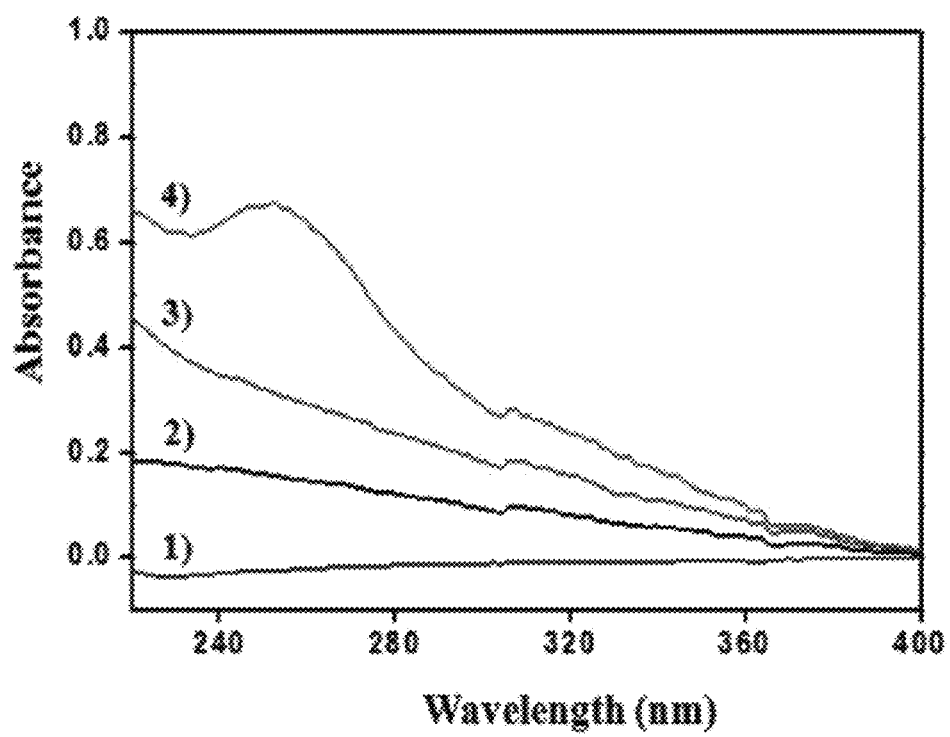
FIG. 4 illustrates a result obtained by measuring the nitric oxide releasing particles according to the exemplary embodiment of the present invention using ultraviolet-visible (UV-Vis) spectroscopy.
Figure 5:
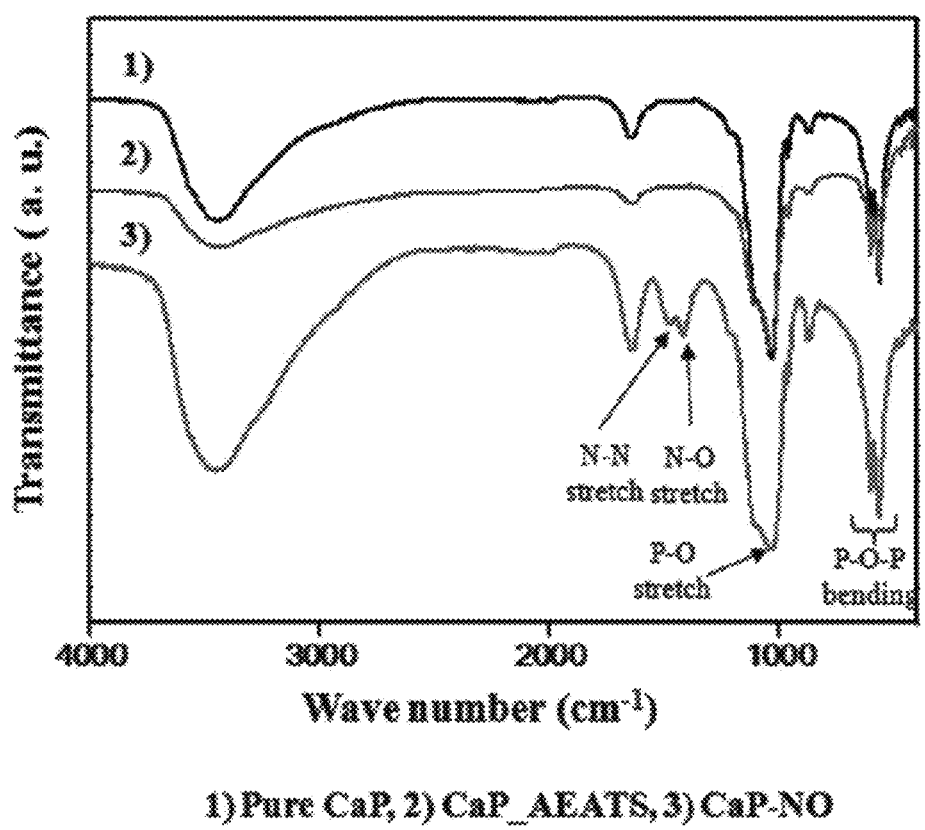
FIG. 5 illustrates a result obtained by measuring the nitric oxide releasing particles according to the exemplary embodiment of the present invention using Fourier transform infrared (FT-IR) spectroscopy.

3. Ultraviolet-Visible (UV-Vis) Spectroscopy and Fourier Transform Infrared (FT-IR) Spectroscopy FIGS. 4 and 5 illustrate results obtained by observing nitric oxide releasing particles through UV-Vis spectroscopy and FT-IR spectroscopy. As a result, it was confirmed that a specific peak due to nitric oxide was formed, and thus, release of nitric oxide may be confirmed. A specific signal of nitric oxide was observed in a wavelength range of 1300 to 1700 $cm^{-1}$ through FT-IR spectroscopy. It was confirmed through UV-Vis spectroscopy that a specific peak of nitric oxide was shown at 250 nm.

4. Analysis of Zeta Potential

Figure 6:
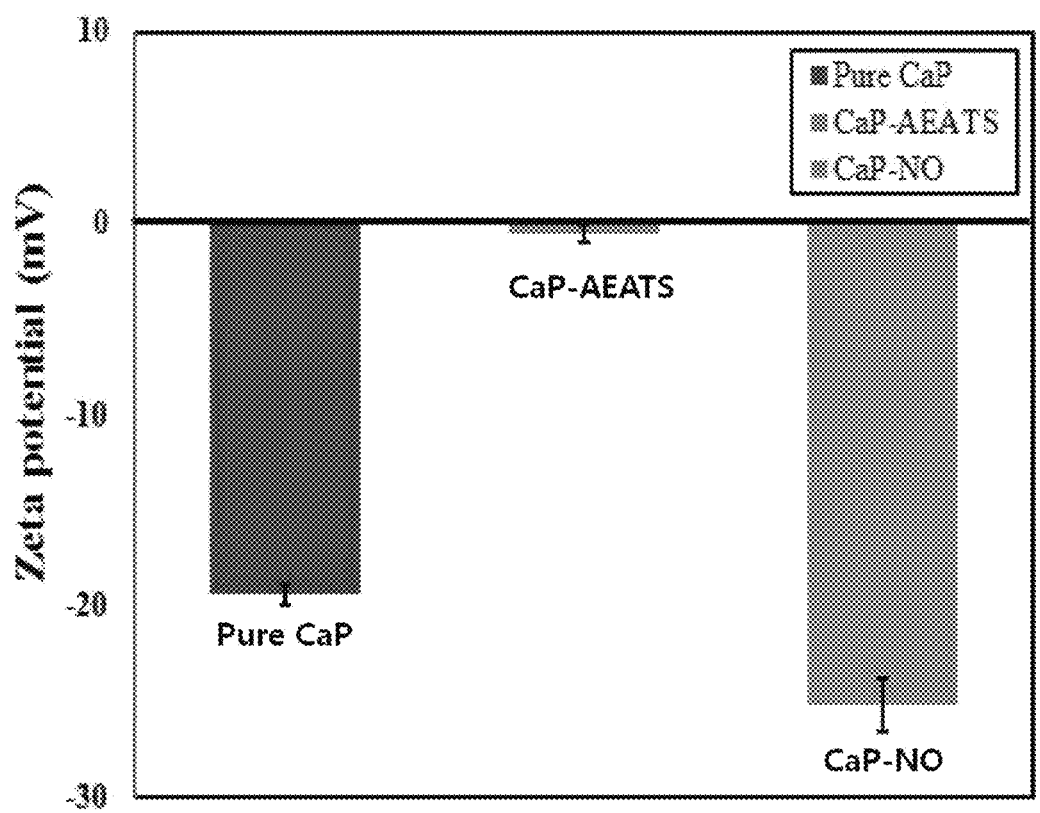
FIG. 6 illustrates a result obtained by measuring a zeta potential of the nitric oxide releasing particles according to the exemplary embodiment of the present invention using a zeta potentiometer.

FIG. 6 illustrates a result obtained by measuring zeta potentials of pure CaP, CaP-AEATS, and CaP—NO, respectively, using a zeta potentiometer. As a result, after introduction of AEATS, CaP-AEATS was negatively charged weakly, and after introduction of nitric oxide, CaP—NO was strongly negatively charged again. Therefore, whether or not nitric oxide existed may be confirmed.

5. Detection of Calcium Ion Depending on pH (Arsenazo Assay)

Figure 7:
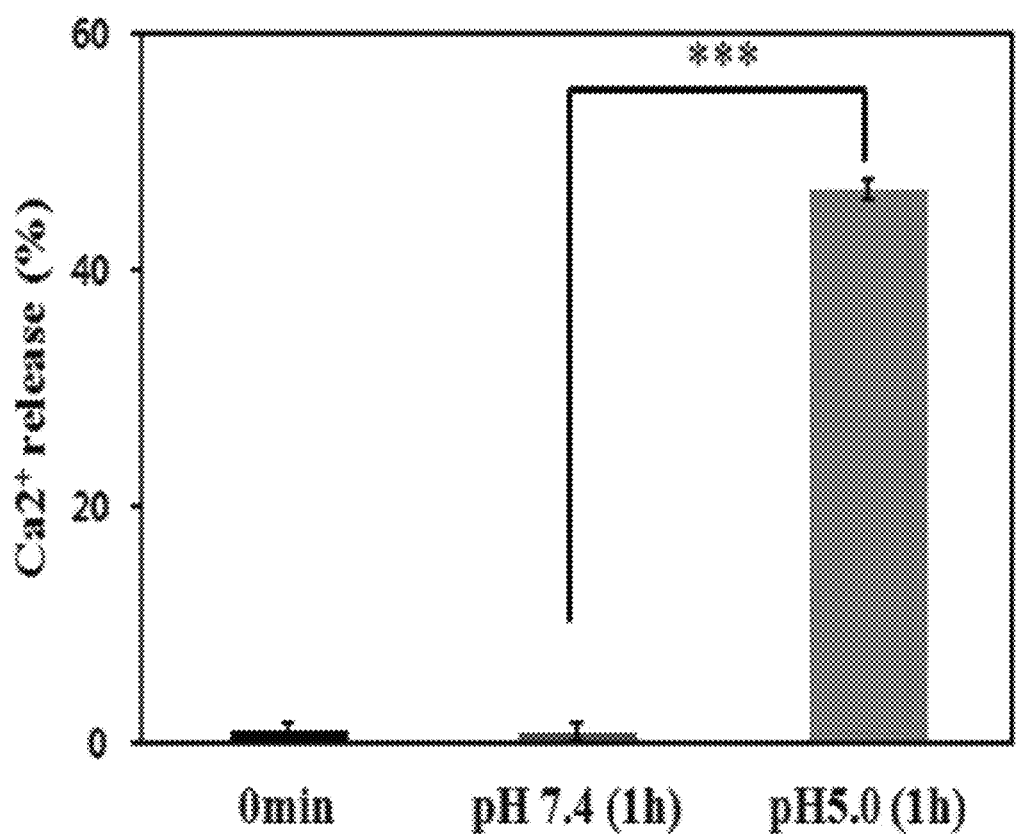
FIG. 7 illustrates a result obtained by measuring the nitric oxide releasing particles according to the exemplary embodiment of the present invention using a calcium ion detection method.

FIG. 7 illustrates a calcium ion detection result by Arsenazo III complexion method) [Micaylova V Et al., Anal. Chim. Acta, 53(194), 1971]. As a result of confirming biodegradability of hydroxyapatite through detection of calcium ion under a weak acidic condition, it was confirmed that the calcium ion was not detected at pH 7.4, but the calcium ion (49.3%) was detected at pH 5.

6. Release of Nitric Oxide Depending on pH (Sievers NOA)

Figure 8:
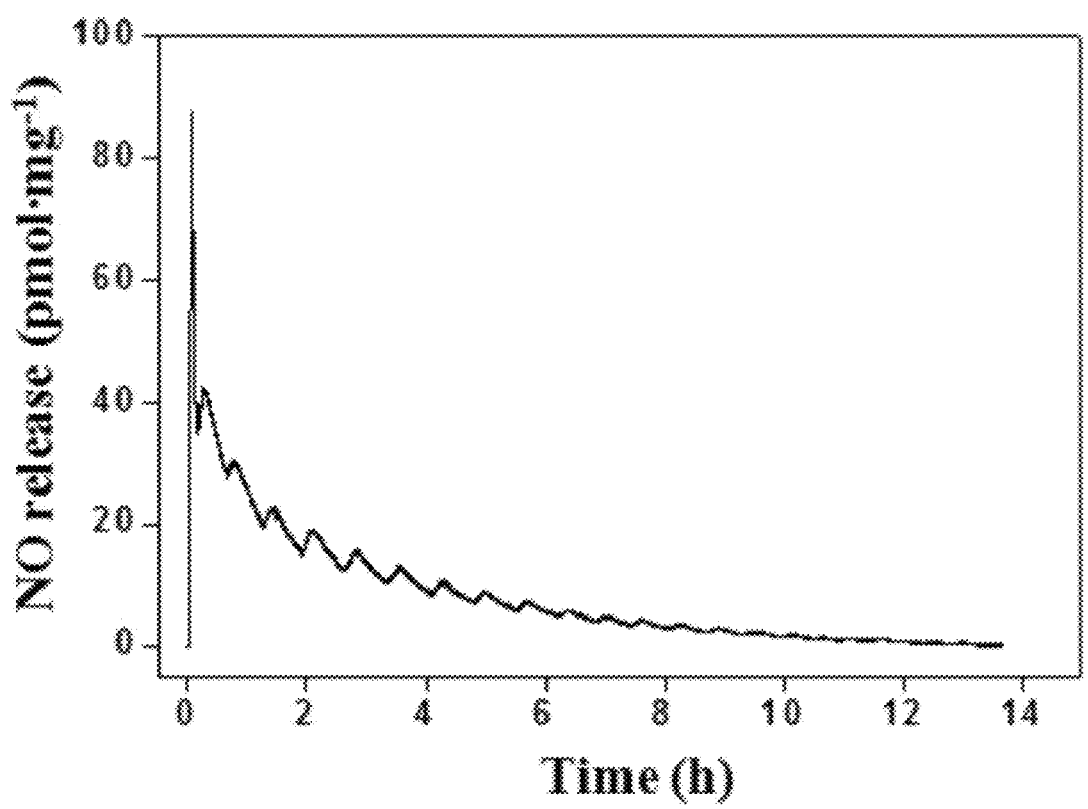
FIG. 8 illustrates a result obtained by measuring a nitric oxide release behavior of N-(N-(2-aminoethyl)-3-aminopropyl trimethoxysilane (AEATS) according to the exemplary embodiment of the present invention using a nitric oxide detector at pH 7.4.
Figure 9:
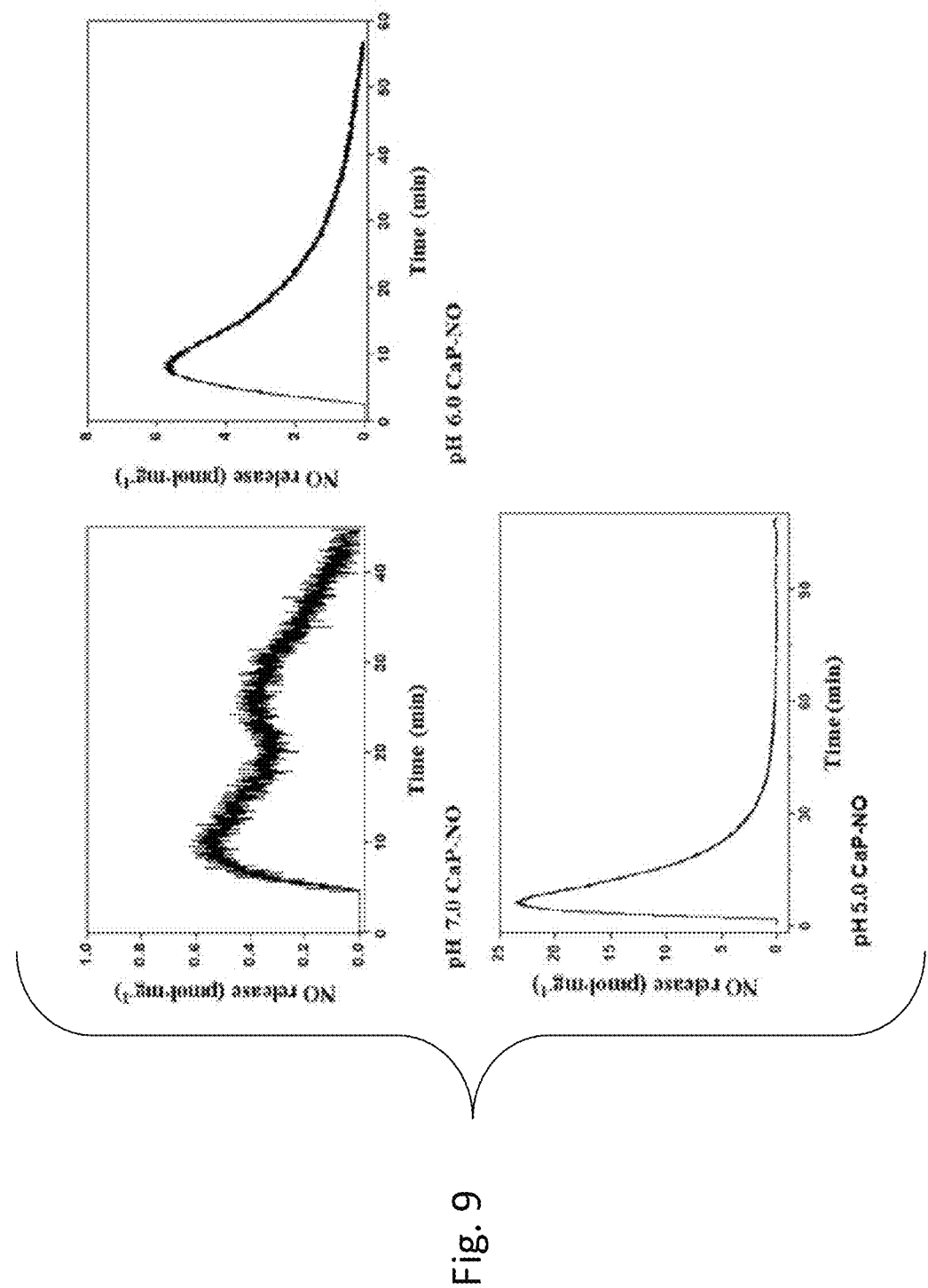
FIG. 9 illustrates a result obtained by measuring a nitric oxide release behavior of CaP—NO according to the exemplary embodiment of the present invention using and a nitric oxide detector depending on a change in pH.
Figure 10:
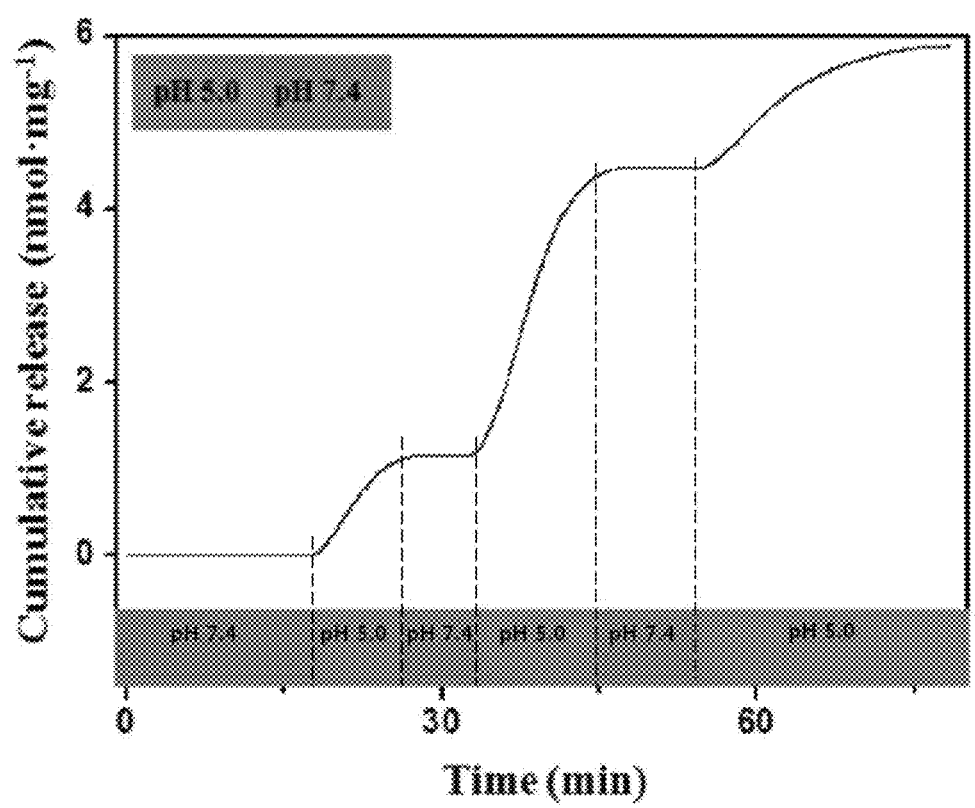
FIG. 10 illustrates a result obtained by measuring a nitric oxide release behavior of CaP—NO according to the exemplary embodiment of the present invention while alternately changing pH between pH 7.4 and pH 5.0 using a nitric oxide detector depending on a change in pH.
Figure 11:
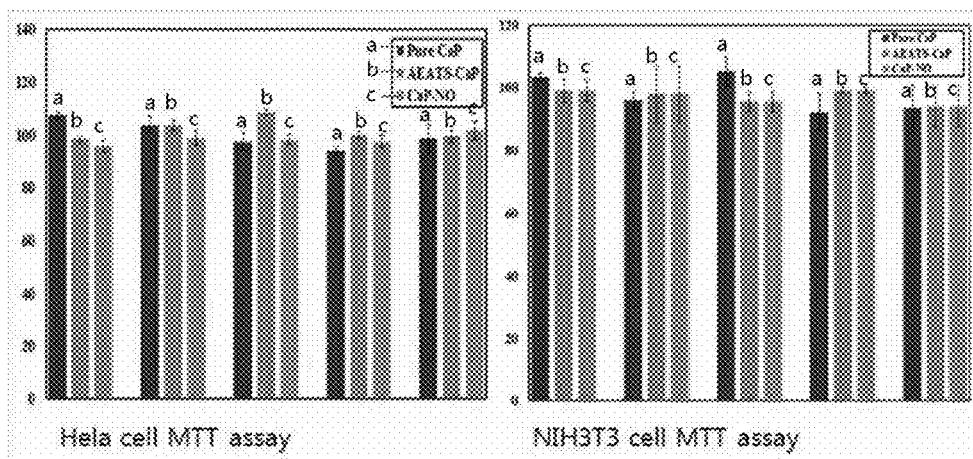
FIG. 11 illustrates a result obtained by measuring biocompatibility of the nitric oxide releasing particles according to the exemplary embodiment of the present invention using MTT assay.

FIGS. 8 to 10 illustrate results obtained using a nitric oxide detector (Sievers NOA, GE analytical instruments, USA) in order to confirm a nitric oxide release behavior of the synthesized CaP—NO depending on the change in pH. FIG. 8 illustrates a result of observing the nitric oxide release behavior after adding 1 mg of AEATS to 40 ml of Dulbecco's Phosphate-Buffered Saline (DPBS, pH 7.4). As a result, it was confirmed that a large amount of nitric oxide was released. FIG. 9 illustrates a result of confirming a nitric oxide release behavior of CaP—NO depending on a change in pH. As a result of observing the nitric oxide release behavior after adding 1 mg of CaP—No to 40 ml of DPBS (pH 7.0, 6.0, and 5.0), it was confirmed that as the pH was decreased, hydroxyapatite was rapidly decomposed. As illustrated in FIG. 10, nitric oxide was not released from CaP—NO at pH 7.4, but when the pH was decreased to 5 using HCl, nitric oxide was released from CaP—NO. When the pH was increased to 7.4 again, nitric oxide was not released, and as a result of observing the nitric oxide release behavior while repeatedly changing the pH, it was confirmed that when the pH was 5, nitric oxide was released.

7. Cytotoxicity Test (MTT Assay) Using Hela Cell and NIH 3T3 Cell

An MTT assay is an assay using capacity of mitochondria reducing 3-(4,5-dimethylthiazol-2-yl)-2,5-diphenyltetrazolium bromide (MTT) tetrazolium (yellow color), a water-soluble matrix, to water-insoluble MTT formazan (jade green color) by dehydrogenase activity. MTT formazan has the maximum absorbance at a wavelength of 540 nm, and absorbance measured at 540 nm reflects a concentration of alive cells in which metabolism was actively carried out.

After a control sample (only cell), Pure CaP, AEATS-CaP, and CaP—NO were each prepared at amounts of 0.01, 0.05, 0.1, 0.5, and 1 mg/ml, added to plates in which Hela and NIH3T3 cells (8000 cells) were seeded, respectively, and stored in an incubator for 24 hours, cytotoxicity was confirmed. As a result, a cell survival rate was 95% or more as compared to the control sample, which indicates that CaP—NO did not cause toxicity.

The method of selectively releasing nitric oxide using the nitric oxide releasing particles according to the present invention may stably deliver nitric oxide to a desired site, and induce release of nitric oxide by a change in pH, thereby making it possible to improve a therapeutic effect while preventing a loss of nitric oxide.

Further, other drugs may be additionally added to the nitric oxide releasing particles according to the present invention, and thus, it is expected that the therapeutic effect of nitric oxide in addition to the therapeutic effect of the drug may be exhibited through dual delivery.

Hereinabove, although the present invention is described by specific matters, exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described embodiments, and the following claims as well as all modified equally or equivalently to the claims are intended to fall within the scope and spirit of the invention.

What is claimed is:

1. A nitric oxide releasing particle prepared by a method comprising:
   a) performing a reaction of calcium phosphate and a silane coupling agent containing a secondary amine group at pH 7 to 11, thereby obtaining a product containing the secondary amine group; and
   b) reacting the product of step a) with nitric oxide, thereby introducing a diazeniumdiolate functional group into the product of step a).

2. The nitric oxide releasing particle of claim 1, wherein the silane coupling agent is represented by the following Chemical Formula 1:

[Chemical Formula 1]

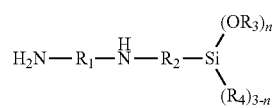

wherein $R_1$ and $R_2$ are each independently a (C1-C12) alkylene group, $R_3$ and $R_4$ are each independently a (C1-C4)alkyl group, and n is 1 to 3.

3. The nitric oxide releasing particle of claim 1, wherein the calcium phosphate is hydroxyapatite ($Ca_{10}(PO_4)_6(OH)_2$).

4. A method of preparing nitric oxide releasing particles of claim 1, the method comprising:
   a) forming calcium phosphate in a solution in which a silane coupling agent containing a secondary amine group is contained; and
   b) injecting nitric oxide gas thereinto to form a diazeniumdiolate functional group.

5. The method of claim 4, wherein the calcium phosphate in step a) is formed by mixing any one phosphate salt selected from phosphoric acid ($H_3PO_4$), sodium dihydrogen phosphate ($NaH_2PO_4$), sodium hydrogen phosphate ($Na_2HPO_4$), potassium dihydrogen phosphate ($KH_2PO_4$), potassium hydrogen phosphate ($K_2HPO_4$), ammonium dihydrogen phosphate ($NH_4H_2PO_4$), and ammonium hydrogen phosphate (($NH_4)_2HPO_4$) and any one calcium salt selected from calcium nitrate ($Ca(NO_3)_2$), calcium carbonate ($CaCO_3$), calcium chloride ($CaCl_2$), calcium hydroxide ($Ca(OH)_2$), and calcium acetate ($Ca(CH_3COO)_2$) with each other.

6. The method of claim 4, wherein a pH in step a) is adjusted to 7 to 11.

7. A method of selectively releasing nitric oxide, wherein nitric oxide is released by adjusting a pH of the nitric oxide releasing particle of claim 1 to 5.0 to 7.4.

* * * * *